(12) United States Patent
Mane et al.

(10) Patent No.: US 9,969,691 B2
(45) Date of Patent: May 15, 2018

(54) POLYMORPHIC FORMS OF PITAVASTATIN SODIUM

(71) Applicant: LUPIN LIMITED, Mumbai (IN)

(72) Inventors: Narendra Dattatray Mane, Maharashtra (IN); Sagar Purushottam Nehate, Maharashtra (IN); Himanshu Madhav Godbole, Maharashtra (IN); Girij Pal Singh, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days. days.

(21) Appl. No.: 15/324,972

(22) PCT Filed: Jul. 8, 2015

(86) PCT No.: PCT/IB2015/055166
§ 371 (c)(1),
(2) Date: Jan. 9, 2017

(87) PCT Pub. No.: WO2016/005919
PCT Pub. Date: Jan. 14, 2016

(65) Prior Publication Data
US 2017/0217894 A1 Aug. 3, 2017

(30) Foreign Application Priority Data
Jul. 9, 2014 (IN) .................. 2246/MUM/2014

(51) Int. Cl.
*C07D 215/14* (2006.01)
(52) U.S. Cl.
CPC ........ *C07D 215/14* (2013.01); *C07B 2200/13* (2013.01)
(58) Field of Classification Search
CPC ........................... C07D 215/04; C07B 2200/13
See application file for complete search history.

(56) References Cited

U.S. PATENT DOCUMENTS

| | | | |
|---|---|---|---|
| 5,753,675 A | 5/1998 | Wattanasin | |
| 5,856,336 A | 1/1999 | Fujikawa et al. | |
| 5,872,130 A | 2/1999 | Fujikawa et al. | |
| 8,487,105 B2 * | 7/2013 | Reddy ............ | C07D 215/14 546/173 |

FOREIGN PATENT DOCUMENTS

| | | |
|---|---|---|
| EP | 0304063 A2 | 2/1989 |
| EP | 1099694 A1 | 5/2001 |
| WO | 2010/089770 A2 | 8/2010 |

OTHER PUBLICATIONS

International Search Report and Written Opinion for corresponding International Application No. PCT/IB2015/055166, dated Sep. 11, 2015, 17 pages.
Suzuki M. et al.: "Synthesis and Biological Evaluations of Quinoline-Based HMG-CoA Reductase Inhibitors", Bioorganic & Medicinal Chemistry, Pergamon, GB, vol. 9, No. 10, Oct. 1, 2001 (Oct. 1, 2001), pp. 2727-2743, XP027388345.
Takahashi et al. "Synthesis of an Artificial HMG-CoA Reductase Inhibitor NK-104 via a Hydrosilylation-Cross-Coupling Reaction," Bull. Chem. Soc. Japan (1995), vol. 68, pp. 2649-2656.
Miyachi et al., "A Novel Synthetic Method of HMG-CoA Reductase Inhibitor NK-104 via a Hydroboration-Cross Coupling Sequence," Tetrahedron Letters (1993), vol. 34, pp. 8267-8270.

\* cited by examiner

*Primary Examiner* — D Margaret M Seaman
(74) *Attorney, Agent, or Firm* — Merchant & Gould P.C.

(57) ABSTRACT

The present invention is directed to polymorphic forms of Pitavastatin sodium and processes for preparation of the same.

7 Claims, 3 Drawing Sheets

POLYMORPHIC FORMS OF PITAVASTATIN SODIUM

FIELD OF THE INVENTION

The present invention relates to novel polymorphic forms of Pitavastatin Sodium and hydrates and/or solvates thereof and processes for the preparation of the same.

BACKGROUND AND THE PRIOR ART

Pitavastatin is a cholesterol lowering agent of the class of HMG-CoA reductase inhibitor. The HMG-CoA reductase enzyme catalyzes the conversions of HMG-CoA to mevalonate. Inhibitors of HMG-CoA reductase are commonly referred to as "statins." Statins are therapeutically effective drugs used for reducing low density lipoprotein (LDL) particle concentration in the blood stream of patients at risk for cardiovascular disease.

Pitavastatin is one of the synthetic statins which is chemically known as (3R, 5S, 6E)-7-[2-cyclopropyl-4-(4-fluorophenyl) quinoline-3-yl]-3,5-dihydroxy-6-heptenoic acid represented by structural formula (1):

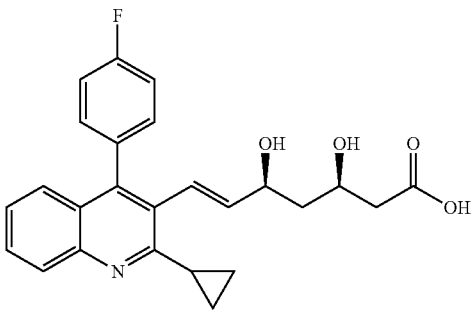

Formula (1)

Pitavastatin and its pharmaceutically acceptable salts are described in U.S. Pat. No. 5,753,675 patent and U.S. Pat. No. 5,856,336 patent, respectively.

Processes for the preparation of Pitavastatin are well documented in the literature. European patents, EP 0304063 and EP 1099694 and reports by Miyachi et al (Tetrahedron Letters (1993) vol. 34, pages 8267-8270) and Takahashi et al (Bull. Chem. Soc. Japan (1995) Vol. 68, 2649-2656) describe processes for preparation of Pitavastatin.

U.S. Pat. No. 5,872,130 patent discloses sodium salt of Pitavastatin. This patent, however, is silent about the solid state form of Pitavastatin Sodium.

It is generally known in the art that active pharmaceutical ingredients frequently do not exhibit the range of physical properties that makes them directly suitable for development. One of the approaches that is used to modify the characteristics of drug substances is to employ a salt form of the substance, since salts enable one to modify aqueous solubility, dissolution rate, solution pH, crystal form, hygroscopicity, chemical stability, melting point and even mechanical properties. The beneficial aspects of using salt forms of active pharmaceutical ingredients are well known and represent one of the means to increase the degree of solubility of otherwise intractable substances and to increase bioavailability.

Although the known salts of Pitavastatin like sodium, potassium, magnesium, calcium etc. and their polymorphic forms may address some of the deficiencies in terms of formulated product and its manufacturability. There remains a need for yet further improvement in these properties as well as improvements in other properties such as flowability, and solubility.

Polymorphism is a known phenomenon among pharmaceutical substances. It is commonly defined as the ability of any substance to exist in two or more crystalline phases that have a different arrangement and/or conformation of the molecules in the crystal lattice. Different polymorphic forms of the same pharmaceutically active moiety also differ in their physical properties such as melting point, solubility, chemical reactivity, etc. These properties may also appreciably influence pharmaceutical properties such as dissolution rate and bioavailability.

Further, the discovery of new polymorphic forms and solvates of an active pharmaceutical ingredient provides broader scope to a formulation scientist for formulation optimization, for example by providing a product with different properties, e.g., better processing or handling characteristics, improved dissolution profile, or improved shelf-life. For at least these reasons, there is a need for polymorphs of Pitavastatin salts such as Pitavastatin sodium.

New polymorphic forms and hydrates and/or solvates of a pharmaceutically acceptable salt of Pitavastatin can also provide an opportunity to improve the performance characteristics of a pharmaceutical product.

Therefore, there is a scope to prepare novel polymorphic forms of Pitavastatin sodium and hydrates and/or solvates.

BRIEF DESCRIPTION OF THE PRESENT INVENTION

The present invention is based upon the studies on various polymorphic forms of pitavastatin sodium, which are suitable for therapeutic use as mentioned herein before.

In one aspect, the present invention provides novel polymorphic forms of Pitavastatin sodium and hydrates and/or solvates thereof.

In another aspect, the present invention provides various processes for preparation of novel polymorphic forms of Pitavastatin sodium and hydrates and/or solvates thereof.

Yet in another aspect, the present invention provides pharmaceutical composition comprising an effective amount of novel polymorphic forms of Pitavastatin sodium and their hydrates and/or solvates.

DETAILED DESCRIPTION OF THE INVENTION

Accordingly, the present invention relates to novel polymorphic forms of Pitavastatin sodium.

In an embodiment, the present invention provides novel crystalline Form-I of Pitavastatin sodium.

In accordance with the present invention, the crystalline Form-I of Pitavastatin sodium is a hydrate, preferably monohydrate.

In an embodiment of the invention provides crystalline Form-I of Pitavastatin sodium characterized by a distinctive PXRD pattern. More specifically such a PXRD pattern is characterized by peaks at 9.36, 10.32, 13.33, 14.14, 18.70, 21.18, 21.51, 22.87, 23.27, and 24.90±0.2 degree 2θ.

In another embodiment, the crystalline Form-I of Pitavastatin sodium is further characterized by a PXRD pattern having characteristic peaks at 4.65, 8.44, 9.36, 10.32, 13.33, 14.14, 17.73, 18.70, 19.81, 21.18, 21.51, 22.87, 23.27, and 24.90±0.2 degree 2θ.

Figure 1:
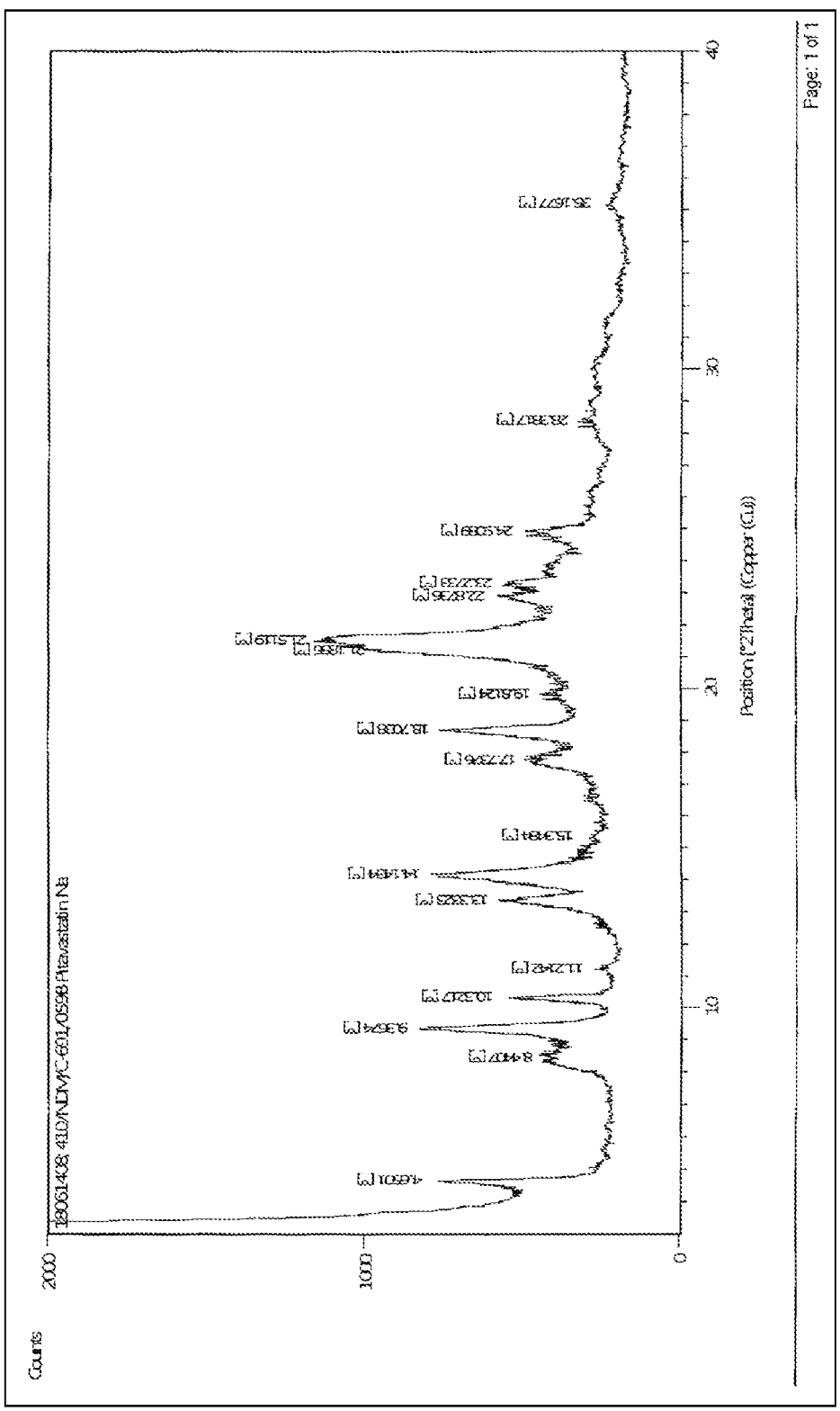
FIG. 1: PXRD pattern of the crystalline form-I of Pitavastatin Sodium.

The PXRD pattern of the crystalline Form-I is shown in FIG. 1.

In yet another embodiment of the present invention provides novel crystalline Form-II of Pitavastatin sodium.

In accordance with the present invention, the crystalline Form-II of Pitavastatin sodium is hydrate, preferably pentahydrate.

In an embodiment of the invention provides crystalline Form-II of Pitavastatin sodium characterized by a distinctive PXRD pattern. More specifically such a PXRD pattern is characterized by peaks at 8.35, 10.00, 13.38, 16.76, 19.02, 20.06, 22.95 and 25.25±0.2 degree 2θ.

In another embodiment, the crystalline Form-II of Pitavastatin sodium is further characterized by a PXRD pattern having characteristic peaks at 4.17, 5.78, 8.35, 10.00, 11.64, 13.38, 14.31, 14.93, 16.76, 17.68, 19.02, 20.06, 20.45, 21.31, 22.30, 22.95, 23.55, 24.76, 25.25, 25.89, 28.32, 29.48 and 30.08±0.2 degree 2θ.

Figure 2:
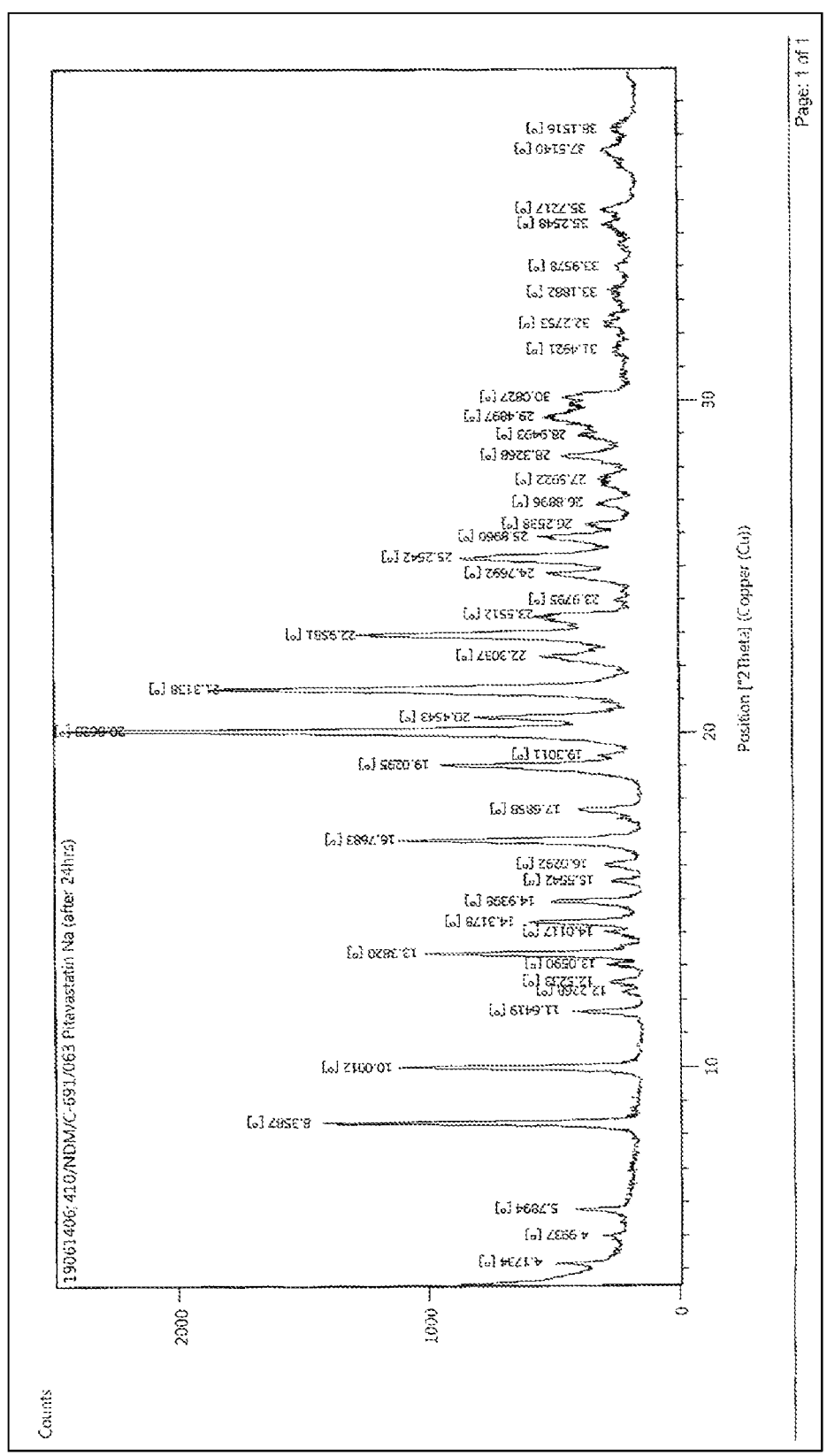
FIG. 2: PXRD pattern of the crystalline form-II of Pitavastatin Sodium.

The PXRD pattern of the crystalline Form-II is shown in FIG. 2.

The crystalline Form-I of Pitavastatin sodium of the present invention is prepared from Pitavastatin acid of the formula (1). The Pitavastatin acid is taken in water and cooled to 0-20° C. temperature, preferably to 5-20° C. temperature, more preferably to 15-20° C. temperature.

Thereafter aqueous sodium hydroxide is gradually added to the reaction mixture at the same temperature. The reaction mixture is stirred for 15-180 min, preferably for 60-120 min, more preferably for 30-45 min, at 0-20° C. temperature, preferably at 5-20° C. temperature, more preferably at 15-20° C. temperature. Thereafter ethyl acetate is added to the reaction mixture. The reaction mixture is stirred for 15-20 min and the layers are separated. The aqueous layer is filtered and acetonitrile is added gradually to the reaction mixture at 0-20° C. temperature, preferably at 5-20° C. temperature, more preferably at 15-20° C. temperature till the precipitation is completed.

The reaction mixture is further cooled to 0-20° C. temperature, preferably to 5-20° C. temperature, more preferably to 5-8° C. temperature and stirred for 1-8 hours, preferably for 1-5 hours, more preferably for 2-3 hours. The precipitated solid is collected by filtration and is dried at 40-80° C. temperature, preferably at 40-60° C. temperature, more preferably at 45-50° C. temperature under vacuum for 5-24 hours, preferably for 5-18 hours, more preferably for 10-12 hours to afford Pitavastatin Sodium crystalline Form-I.

The crystalline Form-II of Pitavastatin sodium of the present invention is prepared from Pitavastatin acid of the formula (1). The Pitavastatin acid is taken in water and cooled to 0-20° C. temperature, preferably to 5-20° C. temperature, more preferably to 15-20° C. temperature. Thereafter aqueous sodium hydroxide is gradually added to the reaction mixture at the same temperature. The reaction mixture is stirred for 15-180 min, preferably for 60-120 min, more preferably for 30-45 min, at 0-20° C. temperature, preferably at 5-20° C. temperature, more preferably at 15-20° C. temperature. Thereafter ethyl acetate is added to the reaction mixture. The reaction mixture is stirred for 15-20 min and the layers are separated. The aqueous layer is filtered and acetonitrile is added gradually to the reaction mixture at 0-20° C. temperature, preferably at 5-20° C. temperature, more preferably at 15-20° C. temperature till the precipitation is completed.

The reaction mixture is further cooled to 0-20° C. temperature, preferably to 5-20° C. temperature, more preferably to 5-8° C. temperature and stirred for 1-8 hours, preferably for 1-5 hours, more preferably for 2-3 hours. The precipitated solid is collected by filtration and dried at 40-80° C. temperature, preferably at 40-60° C. temperature, more preferably at 45-50° C. temperature under vacuum for 5-24 hours, preferably for 5-18 hours, more preferably for 10-12 hours. The dried solid is kept at 25-30° C. temperature and 60±5 RH (relative humidity) for 18-24 hours to afford Pitavastatin Sodium crystalline Form-II.

Alternatively, the crystalline Form-II is also prepared by drying the wet solid obtained after filtration.

In yet another embodiment, the Pitavastatin Sodium Form-I is converted to Pitavastatin Sodium Form-II.

In an embodiment, the present invention provides an amorphous form of Pitavastatin sodium.

In yet another embodiment, the present invention provides an amorphous form of Pitavastatin sodium characterized by PXRD.

Figure 3:
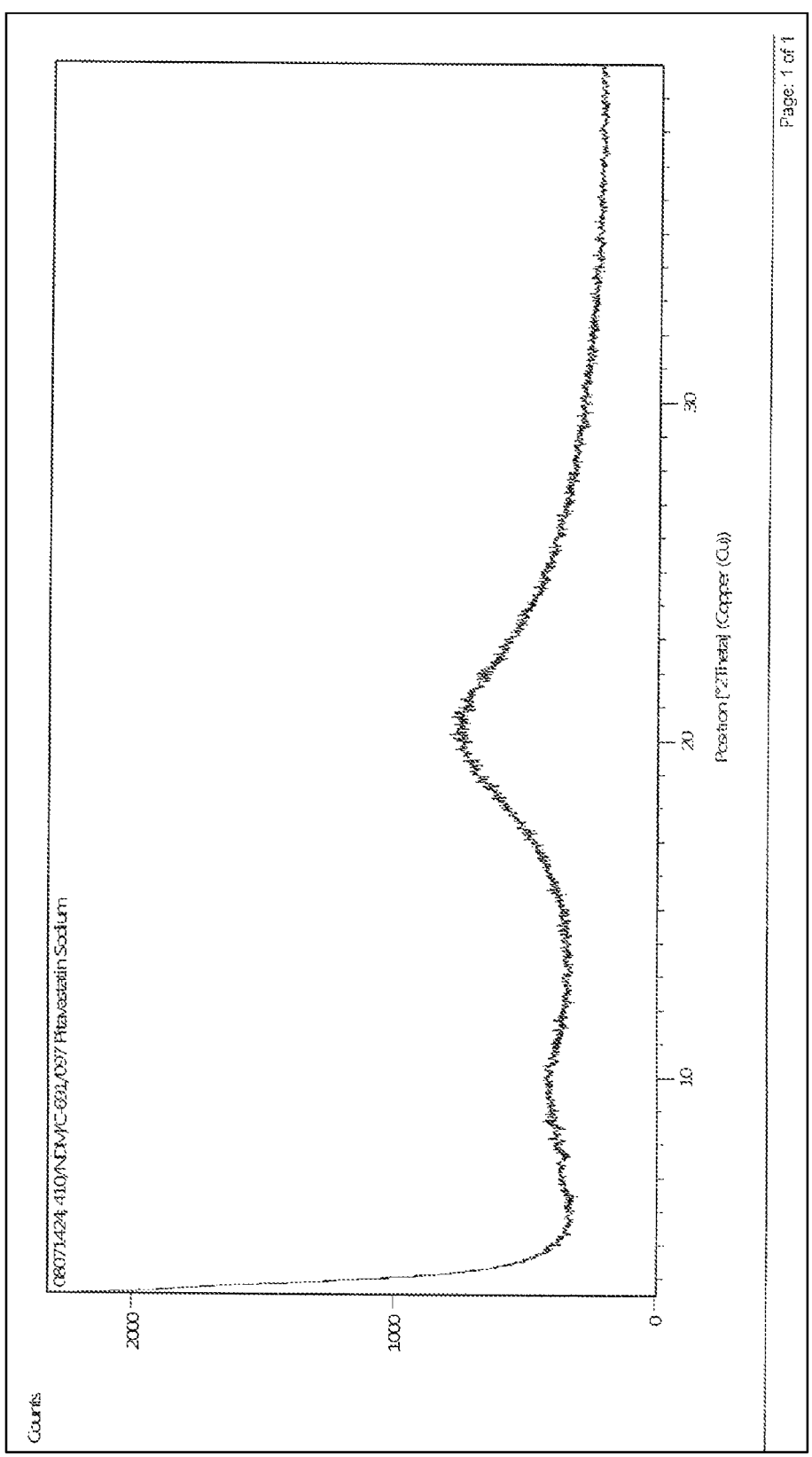
FIG. 3: PXRD pattern of the amorphous form of Pitavastatin Sodium.

The PXRD pattern of an amorphous form of Pitavastatin sodium is shown in FIG. 3.

The amorphous form of Pitavastatin sodium is prepared from Pitavastatin sodium Form-I and/or Form-II of the present invention. The Pitavastatin Form-I and/or Form-II is taken in an alcoholic solvent and the solvent is removed. Suitable techniques for solvent removal include using a rotational distillation device such as a rotary evaporator instrument, spray drying, agitated thin film drying, freeze drying (lyophilization), and the like.

The alcoholic solvent used for the preparation of the amorphous form is selected from the group of C1 to C5 straight or branched chain alcohol. Suitable solvents include, although not limited to, ethanol, methanol, isopropanol and the like.

The Pitavastatin acid, as used in the present invention, can be prepared lay a process generally known in the art or by a novel process.

The Form-I, Form-II and amorphous form of Pitavastatin sodium of the present invention is used as HMG-CoA reductase inhibitors.

Another aspect of the present invention is to provide pharmaceutical compositions comprising an effective amount of crystalline Form-I or Form-II or an amorphous form of Pitavastatin sodium and a pharmaceutical acceptable carrier.

These polymorphic forms may be used as single component or as mixtures with other crystalline form or an amorphous form.

The polymorphic forms of Pitavastatin sodium of the present invention may be used to prepare pharmaceutical composition for the reduction of elevated total cholesterol (TC), low-density lipoprotein cholesterol (LDL-C), apolipoprotein B (Apo B), triglycerides (TG) and to increase high-density lipoprotein cholesterol (HDL-C). Such pharmaceutical composition can be prepared by the methods known in the literature.

The present invention is further illustrated with the following non-limiting examples.

Example-1: Preparation of Pitavastatin Sodium (Form-I)

A mixture of 40.0 gm Pitavastatin acid and 120 ml water was cooled to 15-20° C. temperature. Thereafter aqueous solution of sodium hydroxide (4.0 gm) in water (20 ml) was added to the reaction mixture. The reaction mixture was stirred for 30-45 min at 15-20° C. temperature. Ethyl acetate (80 ml) was added into the reaction mixture at 15-20° C. temperature, stirred for 15-20 min and the layers were separated. The aqueous layer was filtered and acetonitrile (1200 ml) was gradually added to the aqueous layer under stirring till the precipitation was completed. The reaction mixture was cooled to 5-8° C. temperature and stirred for 2-3 hours at 5-8° C. temperature. The precipitated solid was filtered, washed with acetonitrile (40 ml) and dried at 45-50° C. temperature under vacuum for 10-12 hours to afford the title compound (28.0 gm).

Yield (w/w): 0.70 (66.0%)
HPLC purity: 99.70%

Example-2: Preparation of Pitavastatin Sodium (Form-II)

A mixture of 40.0 gm of Pitavastatin acid and 120 ml of water was cooled to 15-20° C. temperature under stirring. Thereafter aqueous solution of sodium hydroxide (4.0 gm) in water (20 ml) was added to the reaction mixture. The reaction mixture was stirred for 30-45 min at 15-20° C. temperature. Ethyl acetate (80 ml) was added to the reaction mixture at 15-20° C. temperature, stirred for 15-20 min and the layers were separated. The aqueous layer was filtered and acetonitrile (1200 ml) was gradually added to the aqueous layer under stirring till the precipitation was completed. The reaction mixture was cooled to 5-8° C. temperature and stirred for 2-3 hours at 5-8° C. temperature. The precipitated solid was filtered, washed with acetonitrile (40 ml) and dried at 45-50° C. temperature under vacuum for 10-12 hours and kept in a petri dish at 25-30° C. and 60±5 RH (relative humidity) for 18-24 hours to afford the title compound (31.6 gm).

Yield (w/w): 0.79 (65.8%)
HPLC purity: 99.70%

Example-3: Preparation of Pitavastatin Sodium Amorphous

Pitavastatin sodium (3.0 gm) and ethanol (60 ml) were taken in a round bottomed flask at 25-30° C. temperature. The reaction mixture was filtered and the solvent was distilled off on rotatory evaporator under vacuum maintaining bath temperature at 45-50° C. temperature. Thereafter the reaction mixture was degassed under vacuum for 2-3 hours to afford the title compound (2.8 gm).

HPLC purity: 99.70%.

The invention claimed is:

1. Crystalline Form-II of Pitavastatin sodium, wherein the crystalline Form-II of Pitavastatin sodium has an X-ray powder diffraction pattern having characteristic peaks expressed in degrees 2θ (±0.2° 2θ) at 8.35, 10.00, 13.38, 16.76, 19.02, 20.06, 22.95 and 25.25.

2. Crystalline Form-II of Pitavastatin sodium, wherein the crystalline Form-II of Pitavastatin sodium has an X-ray powder diffraction pattern having characteristic peaks expressed in degrees 2θ (±0.2° 2θ) at 4.17, 5.78, 8.35, 10.00, 11.64, 13.38, 14.31, 14.93, 16.76, 17.68, 19.02, 20.06, 20.45, 21.31, 22.30, 22.95, 23.55, 24.76, 25.25, 25.89, 28.32, 29.48 and 30.08.

3. The crystalline Form-II of Pitavastatin sodium as claimed in claim 1, wherein the crystalline Form-II of Pitavastatin sodium has an X-ray powder diffraction pattern substantially same as that shown in FIG. 2.

4. The crystalline Form-II of Pitavastatin sodium as claimed in claim 1, wherein the Form-II is in the form of pentahydrate.

5. A process for the preparation of crystalline Form-II of Pitavastatin sodium, which comprises the steps of:
  (a) reacting pitavastatin acid with aqueous sodium hydroxide solution;
  (b) adding acetonitrile to the solution obtained in step (a);
  (c) isolating the solid; and
  (d) exposing the solid isolated in above step (c) to an atmosphere with relative air humidity at about 60% to yield crystalline Form-II.

6. The process according to claim 5, wherein the solid in step (c) is isolated at 0-20° C.

7. The process according to claim 5, wherein the solid isolated in step (c) is exposed to relative air humidity at about 60% for 18-24 hours.

* * * * *